(12) United States Patent
Van Duuren et al.

(10) Patent No.: US 10,520,488 B2
(45) Date of Patent: Dec. 31, 2019

(54) METHOD AND MEASURING DEVICE FOR DETERMINATION OF THE GROWTH RATE OF BIOFILM

(71) Applicant: Helmholtz-Zentrum fuer Infektionsforschung GmbH, Braunschweig (DE)

(72) Inventors: Jost Van Duuren, Saarbruecken (DE); Blanka Karge, Braunschweig (DE); Christoph Wittmann, Saarbruecken (DE); Mark Broenstrup, Braunschweig (DE)

(73) Assignee: Helmholtz-Zentrum fuer Infektionsforschung GmbH, Braunschweig (DE)

( * ) Notice: Subject to any disclaimer, the term of this patent is extended or adjusted under 35 U.S.C. 154(b) by 165 days.

(21) Appl. No.: 15/536,798

(22) PCT Filed: Dec. 18, 2015

(86) PCT No.: PCT/EP2015/080540
§ 371 (c)(1),
(2) Date: Jun. 16, 2017

(87) PCT Pub. No.: WO2016/097316
PCT Pub. Date: Jun. 23, 2016

(65) Prior Publication Data
US 2017/0350875 A1    Dec. 7, 2017

(30) Foreign Application Priority Data
Dec. 18, 2014 (EP) .................. 14198747

(51) Int. Cl.
*G01N 33/483* (2006.01)
*G01N 27/04* (2006.01)
*C12Q 1/02* (2006.01)

(52) U.S. Cl.
CPC .......... *G01N 33/4836* (2013.01); *C12Q 1/02* (2013.01); *C12Q 1/025* (2013.01); *G01N 27/041* (2013.01); *G01N 2333/21* (2013.01)

(58) Field of Classification Search
None
See application file for complete search history.

(56) References Cited

U.S. PATENT DOCUMENTS

| | | | |
|---|---|---|---|
| 2004/0152067 A1* | 8/2004 | Wang | G01N 33/5005 435/4 |
| 2012/0067744 A1 | 3/2012 | Vincent | |
| 2012/0142031 A1 | 6/2012 | Xu | |

FOREIGN PATENT DOCUMENTS

| | | |
|---|---|---|
| WO | 2004/010102 A2 | 1/2004 |
| WO | 2005/047482 A2 | 5/2005 |
| WO | 2005/077104 A2 | 8/2005 |

OTHER PUBLICATIONS

Welch et al., "A Method for Quantitative Determination of Biofilnn Viability", Journal of Functional Biomaterials, vol. 3, pp. 418-431 (Year: 2012).*
Gottschamel et al; "Development of a Disposable Microfluidic Biochip for Multiparameter Cell Population Vleasurements"; Analytical Chemistry, vol. 81, No. 20, Oct. 15, 2009, pp. 8503-8512.
Richter; "On-Chip Monitoring of Fungal Biofilms Using a Lab-on-a-Chip"; Jun. 5, 2008, retrieved from the internet.
Munoz-Berbel et al.; "On-chip impedance measurements to monitor biofilm formation in the drinking water distribution network"; Sensors and Actuators B: Chemical: International Journal Devoted to Research and Development of Physical and Chemical Transducers, vol. 118, No. 1-2, 25 Oct. 25, 2006, pp. 129-134.
Zheng et al; "Electrochemical measurements of biofilm developmentusing polypyrrole enhanced flexible sensors"; Sensors and Actuators B: Chemical: International Journal Devoted to Research and Development of Physical and Chemical Transducers, vol. 182, Apr. 1, 2013, pp. 725-732.
Sachsenheimer et al: "Monitoring Biofilm Growth Using a Scalable Multichannel Impedimetric Biosensor", 15th International Conference on Miniaturized Systems for Chemistry and Life Sciences, pp. 1968-1970, Oct. 2-6, 2011.

\* cited by examiner

*Primary Examiner* — Michelle F. Paguio Frising
(74) *Attorney, Agent, or Firm* — W & C IP (57) ABSTRACT

A method for determination of the growth rate of biofilm using an electrical impedance analyses is disclosed. The method comprises the steps of: bringing a culture medium fluid in contact to an electrode structure, having biofilm grown within the fluid culture medium with the biofilm arranged in distance to the electrodes structure, so that the fluid culture medium is placed between the growing biofilm and the electrode structure; measuring the impedance of the electrodes structure over a monitoring time, and determining the growth rate of the biofilm as a function of the reduction rate of the impedance values measured on the electrode structure.

6 Claims, 9 Drawing Sheets

METHOD AND MEASURING DEVICE FOR DETERMINATION OF THE GROWTH RATE OF BIOFILM

FIELD OF THE INVENTION

The invention relates to a method for determination of the growth rate of biofilm using an electrical impedance analysis.

The invention further relates to a measuring device for determining the growth rate of biofilm, said measuring device comprising:
  at least one electrode structure;
  an impedance measuring unit in electrical connection to the electrode structure being provided for measuring the impedance of the electrode structure, and
  at least one receptacle for storing fluid culture medium, wherein the receptacle is arranged for being coupled to the electrode structure such that the fluid culture medium is able to contact the electrode structure.

BACKGROUND OF THE INVENTION

The use of impedance analysis for monitoring microbiological effects is well known.

K. Sachsenheimer, L. Pires, M. Adamek, Th. Schwartz and B. E. Rapp: Monitoring Biofilm Growth using a Scalable Multichannel Impedimetric Biosensor, in: 15th International Conference on Miniaturized Systems for Chemistry and Life Sciences, Oct. 2-6, 2011, Seattle, Wash., USA, pages 1968 to 1970 discloses a multichannel electrochemical impedance spectroscopy (EIS) based biosensor that allows the monitoring of biofilm growth. The bacterial strains (*Pseudomonas aeruginosa, Stenotrophomonas maltophilia*) were monitored for up to 96 hours with the biofilm directly growing on an electrode structure. Said electrode structure comprises a working electrode and a counter electrode on a substrate. The biofilm growth on the electrode structure hinders the charge transfer between the electrodes and therefore increases the measured impedance. The impedance increases over time because of a biofilm growing on the electrode surface. Two electrodes are used to compensate drift effects, with the measurement electrode probe carrying the bacteria and a reference electrode being only exposed to feeding medium.

WO 2005/047482 A2 and WO 2005/077104 A2 disclose a real time electronic cell sensing system comprising an electrode structure and a plurality of receptacles placed on top of the electrode structure. Two or more electrode arrays are fabricated on a non-conducting substrate. The substrate has a surface suitable for cell attachment or growth. The cell attachment or growth on said substrate results in a detectable change in impedance between the electrode structures within each electrode array. For measurement of the cell-substrate impedance, an impedance analyzer is connected to the connection pads of the substrate for measuring the impedance values at specific frequencies.

The impedance is a complex value comprising the ohmic resistance and the reactance. The reactance is the imaginary part of the impedance and provides the value of the capacitance of the electrode structure. Cell Index values are calculated from the measured impedance data. The dimensionless cell index measures the relative change in the electrical impedance at certain frequency (fn). The Cell Index at a given time point t (CI(t)) is calculated as follows:

$$CI(t) = \frac{R(f_n, t) - R(f_n, t_0)}{Z_n}$$

where
  $f_n$ is the frequency that impedance measurement is carried out,
  $R(f_n, t)$ is the measured impedance at frequency $f_n$ at time point t,
  $R(f_n, t_0)$ is the measured impedance at frequency $f_n$ at time point $t_0$, usually $t_0$ is the time when the background is measured),
  $Z_n$ is the corresponding frequency factor of $f_n$.

For example, the xCELLigence® system, which is available from the company ACEA Biosciences, Inc. USA, measures impedance at three discrete frequencies, i.e., f1=10 kHz, f2=25 kHz, and f3=50 kHz. The corresponding frequency factors are Z1=15 Ohm, Z2=12 Ohm, and Z3=10 Ohm, respectively.

The resistance and reactance part of the cell index can be obtained by mathematical transformations. In another example, the cell index can be calculated at each measured frequency by dividing the resistance value and/or the reactance value of the electrode arrays when cells are present on, or attached to the electrodes by the baseline resistance and/or reactance. Hereby, the maximum value in the reactance ratio over the frequencies spectrum can be found or determined. Alternatively a specific value, e.g. the value 1 or the measured value at the start of the experiment, can be subtracted from the value in the reactance ratio.

Further examples for determining the cell index are disclosed in the references WO 2005/047482 A2 and WO 2005/077104 A2 cited above.

WO 2004/010102 A2 discloses an impedance-based apparatus for analyzing cells and particles comprising an upper chamber adapted to receive and retain a cell sample, a lower chamber having at least two electrodes, and a biocompatible porous membrane having a porosity sufficient to allow cells to migrate therethrough. The cells migrating to the lower chamber attach to the electrodes. In another example the microporous membrane and the electrode structure is placed between the upper and lower chamber. Again cells are attaching to the electrode structure and growing on the electrode structure. With increasing cell numbers, the impedance at specific frequencies and the calculated cell index is increasing. Thus, proportionally the capacity decreases with increasing cells adhering on the electrode structure.

Said disclosed cell monitoring apparatus is commercial available under the trademark xCELLigence® RTCA with CIM-Plates and E-plates. Said device is available from the company ACEA Biosciences, Inc. USA.

SUMMARY

An object of the present invention is to provide an improved method and measuring device for the determination of the growth rate of biofilm.

The object is achieved by the method according with the features of claim 1 and the measuring device comprising the features of claim 9. Preferred embodiments are disclosed in the dependent claims.

According to the present invention, the growth rate of the biofilm is determined as a function of the reduction rate of the impedance values measured on the electrode structure with the biofilm not adhering to the electrode structure.

Therefore, the method comprises steps of:
bringing a fluid culture medium in contact to an electrode structure,
having a biofilm grown within the fluid culture medium with the biofilm arranged in distance to the electrode structure, so that the fluid culture medium is placed between the growing biofilm and the electrode structure,
measuring the impedance of the electrode structure over a monitoring time, and
determining the growth rate of the biofilm as a function of the reduction rate of the impedance values measured on the electrode structure.

While the prior art proposes the determination of the surface impedance on an electrode structure having a pair of electrodes with the biofilm growing on the electrodes, the present invention proposes determination of the biofilm growth rate as a function of the dielectric change of the capacitive structure between the biofilm and the electrodes. Due to an increasing dielectric constant of the doublecharged layer caused by biofilm growth, the capacitance increases. This is achieved by placing the culture medium in a fluid form between the electrode structure and the biofilm, so that the biofilm floats on the culture medium and does not directly contact the electrode structure. As a result, the impedance values measured on the electrode structure shows a reduction in relation to the growing rate of the biofilm. When adhering the biofilm on the electrode structure according to the prior art, the impedance values increases with growing biofilm.

The use of a fluid for the culture medium instead of a gel allows the biofilm to float on top of the fluid culture medium in distance to the electrode structure.

Determining the biofilm formation rate as a function of a reduction rate of the impedance values of the electrode structure with the fluid culture medium being placed between the electrode structure and the biofilm has the advantage of a very low standard deviation and an increased distinctiveness of the measurement results with reproducible values. A high number of probes can be measured in parallel within a short time frame.

In a preferred embodiment, the measured impedance values are scaled and the growth rate of the biofilm is determined as function of the reduction rate of the scaled impedance values. By scaling the measured impedance values, normalized impedance values are achieved, so that the influence of the electrical impedance of the measurement device is faded out.

The scaling of the measured impedance values is preferably performed with respect to related reference impedance values measured on the same or similar electrode structure without biofilm. Thus, the measured impedance values on an electrode structure with biofilm are scaled with the related reference impedance value for the same or similar electrode structure without biofilm. The related reference impedance values can be achieved for example before inserting biomass in the fluid culture medium at a first step. Later, after inserting biomass into the fluid culture medium the impedance values are measured and compared with the referenced impedance values measured in the first step before said second step with biomass.

Another option is to provide similar electrode structures, wherein the impedance values are measured on samples with biomass in parallel to samples without biomass and biofilm growing due to biomass within the fluid culture medium, in order to obtain biomass impedance values and related reference impedance values.

Scaling can be taken place by calculating the quotient between the measured biomass impedance values and the related reference impedance values or by subtracting both values.

In a most preferred embodiment, scaled cell index values are determined as a function of the impedance values measured at different frequencies and of related reference impedance values without biofilm. The impedance values for the different frequencies obtained at the same timepoint is then taken into account. For example, the maximum of the impedance values can be considered. The growth rate of the biofilm is determined in proportion to the reduction rate of the said scaled cell index values.

For example, the cell index values provided by the prior art xCELLigence® RTCA available from the company ACEA Biosciences, Inc. can be used for determining the growth rate of the biofilm.

A possible variant of the method provides that the growth rate of the biofilm is determined as a function of the reduction rate of the reactance portion of the measured impedance value. The measured impedance value comprises a reactance portion and a resistance portion. In this preferred embodiment, only the reactance portion of the impedance is considered for determination of the growth rate of the biofilm. The reactance is the imaginary part of the complex impedance providing a value for the capacitance of the electrode structure and the fluid culture medium placed adjacent to the electrode structure with the biofilm growing in the fluid culture medium in distance to the electrode structure. With growing biofilm, the dielectric properties of the biofilm are changing, thus resulting in an increasing capacitance. In the prior art with cells adhering to the electrode structure, the surface impedance is effective with growing cells causing an increasing impedance and ohmic resistance.

Considering only the reactance portion of the impedance has the advantage of highly reliable measurement values with very low standard deviation and increased distinctiveness most likely due to the fact that only the dielectric behaviour of the biofilm is evaluated for monitoring the biofilm growth rate.

In a preferred embodiment, the growth rate of the biofilm is determined after expiration of a specific growth time. Said specific growth time expires at the earliest when a continuous reduction of the impedance values measured of the electrode structure occurs. The specific growth time is preferably set to a time when biofilm starts to grow significantly, e.g. a time when pellicle is formed.

Thus, the change of the impedance values measured on the electrode structure for at least one frequency is monitored over the monitoring time. It had been experimentally noted, that in a first phase, the impedance values and in particular the cell index or reactance first significantly decreases within a short time of approximately 1 to 4 hours. Then, the values are increasing until expiration of the specific growth time. The growth time depends on the biomass and the specific experimental environment. After expiration of the specific growth time, a continuous reduction of the impedance values occurs. After determination of such a continuous reduction of the measured impedance values or related scaled values or cell index values, the expiration of the growth time is determined. Then, the biofilm growth rate can be determined within the time window of the monitoring time said considered time window being after expiration of the growth time. A mathematical function that describes the biofilm formation can be defined, based on which the slope of the reduction (which is equal to the directional cell index) can be calculated within this period. For example, the specific growth time can be set to a value in a range of 30 to 40 hours and preferably 30 to 35 hours after placing fluid culture medium with biomass or growing biofilm in a receptacle arranged on an electrode structure. The growth rate of the biofilm is then determined within a measurement time of for example 5 hours.

The method for determining the growth rate of biofilm makes most preferably use of the xCELLigence® Real-time cell analyzer of ACEA Biosciences, Inc. or with another suitable device comprising an electrode structure and at least one receptacle provided for placing a fluid culture medium with biomass for growing biofilm on the electrode structure according on the prior art or of biofilm arranged in distance to the electrode structure. The electrode structure comprises at least one measurement electrode and one counter electrode. The measuring device comprises an impedance measuring unit for applying a measurement signal with at least one specific frequency on both electrodes of the electrode structure in order to determine the complex impedance on the electrode structure and in particular the related reactance.

Most preferably, the E96 plates provided for the xCELLigence® Real-time cell analyzer are applicable for the determination of the growth rate of biofilm floating on the fluid cell medium.

The impedance values, in particular the reactance, are further evaluated by use of an evaluating unit in order to perform the above mentioned method. The evaluation unit can be for example a data processing unit, e.g. microcontroller, microprocessor or computer having a computer program for performing the evaluation steps as described above. The evaluation unit can also be a field programmable array FPGA providing a hardware device for performing the evaluation steps.

DESCRIPTION OF THE DRAWINGS

The invention is described by use of exemplary embodiments with the enclosed drawings. It shows:

FIG. 8a-c)—Diagram showing the impact of ciprofloxacin on biofilm formation of PA14.

FIG. 9a-c)—Diagram showing the impact of tobramycin on biofilm formation of PA14.

FIG. 10a-c)—Diagram showing the impact of meropenem on biofilm formation of PA14.

DETAILED DESCRIPTION

Figure 1:
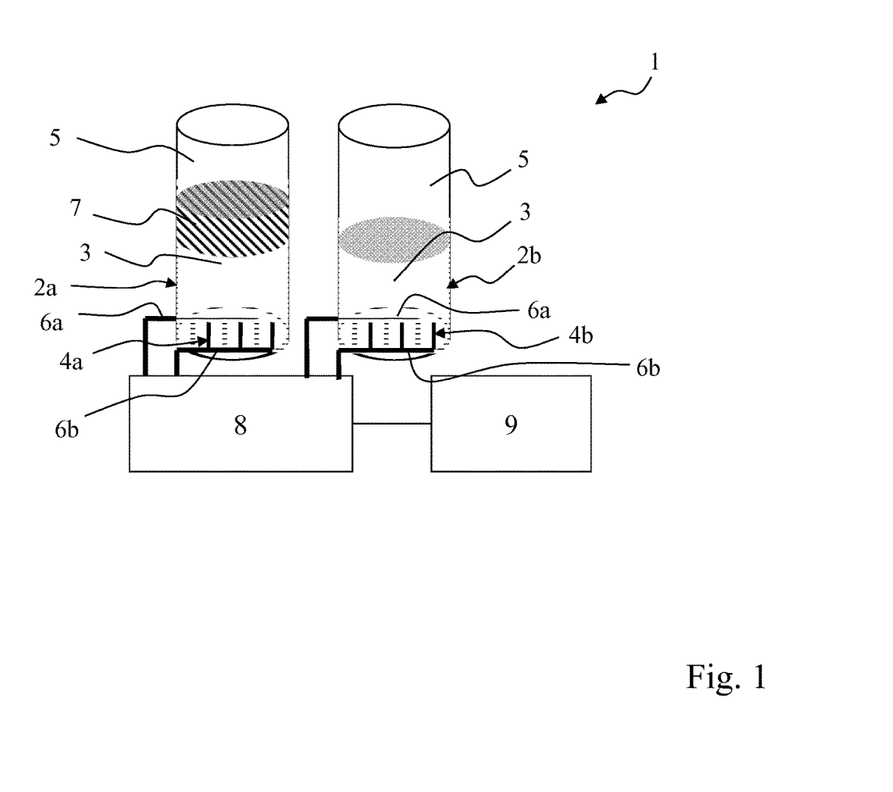
FIG. 1—Block diagram of a first embodiment of a measuring device for determining the biofilm growth rate.

FIG. 1 shows a block diagram of a measuring device 1 for determining the growth rate of biofilm. The measuring device 1 comprises a plurality of receptacles 2a, 2b provided for storing a fluid culture medium 3. Each receptacle 2a, 2b comprising an electrode structure 4a, 4b. In the exemplary embodiment, each electrode structure 4a, 4b is placed at the bottom in the interior space of a chamber 5 formed by a related receptacle 2a, 2b. The receptacles 2a, 2b are placed such, that the fluid culture medium 3 is able to contact the related electrode structure 4a, 4b, wherein one electrode acts as measurement electrode 6a and the other as counter electrode 6b. The electrode structures 4a, 4b each are formed by a pair of comb-type finger electrodes. Each comb-type finger electrode comprising a plurality of fingers extending in the same direction and being placed adjacent to each other like a comb. The pair of comb-type finger electrodes are interdigitating arranged such that the fingers of the pair of comb-type finger electrodes being alternately placed adjacent and in distance from each other such that the adjacent fingers extending in opposite directions from each other.

When injecting biomass into the fluid culture medium 3, a biofilm 7 is growing within the respective chamber 5 and the biofilm 7 is floating on top of the fluid culture medium 3.

Other than in the prior art, by use of fluid culture medium 3 and having the biofilm 7 floating on top of the fluid culture medium 3, the biofilm 7 will not adhere to the electrode structure 4a, 4b.

For all exemplarily described embodiments of the invention and other variants, the impedance of the electrode structures 4a, 4b are each measured by use of an impedance measuring unit 8 in electrical connection to the electrode structures 4a, 4b. In order to measure the impedance, a measuring signal, e.g. a AC sinus wave, is applied to a pair of electrodes of the selected electrode structure 4a, 4b, i.e. the measurement electrode 6a and the counter electrode 6b, and the signal amplitude and phase is then measured. For example when keeping the current constant, the voltage amplitude and phase between the measurement signal and the measured signal will vary as a function of the capacitance. When applying a measuring signal with constant voltage, the current amplitude and the phase angel will vary accordingly. Thus, the impedance measuring unit 8 is arranged to measure the impedance value of a selected electrode structure 4a, 4b. The impedance measuring unit 8 may have a multiplexer for selecting one of the plurality of electrode structures 4a, 4b after the other in order to perform fast impedance measurement for a plurality of receptacles 2a, 2b and their related electrode structures 4a, 4b. The impedance is the sum of the ohmic resistance and the complex reactance:

$$Z = Z_R + Z_C = R + 1/j\omega C$$

where $\omega$ is the frequency of the measurement signal, C the capacity and R the ohmic resistance.

The capacity C is related to the reactance with a kind of exponential function. The capacity C is linear proportional to $\ln(Z)$.

The growth rate of biofilm 7 floating on the fluid culture medium 3 is a function of the reduction rate of the reactance and the increase rate of the capacitance C.

Therefore, the measuring device 1 comprises an evaluation unit 9 arranged for determining the growth rate of biofilm 7 being located in distance to the electrode structure 4a, 4b with the fluid culture medium 3 placed between the electrode structure 4a, 4b and the biofilm 7 as a function of the reduction rate of the impedance values measured on the related electrode structure 4a, 4b by use of the impedance measuring unit 8.

Figure 2:
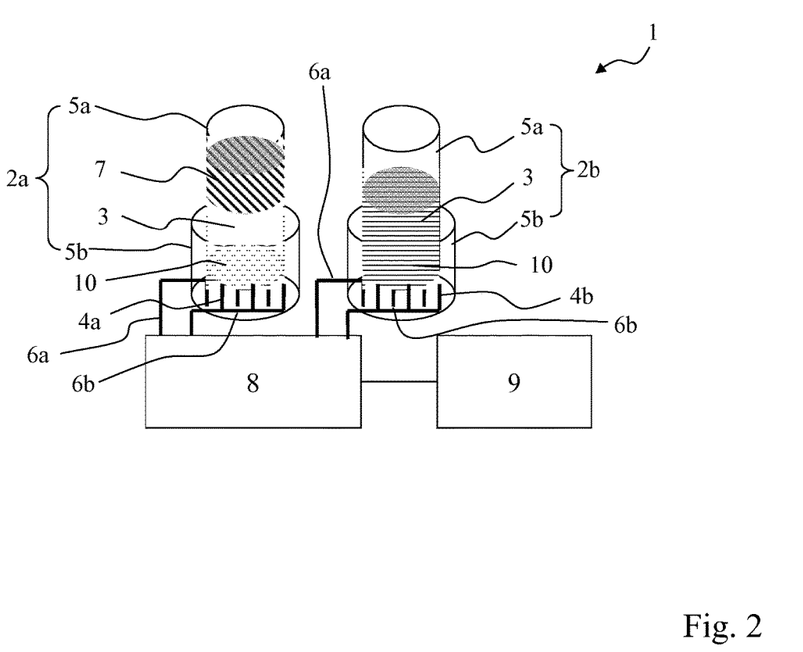
FIG. 2—Block diagram of a second embodiment of a measuring device for determining the biofilm growth rate comprising a microporous membrane.

FIG. 2 shows a schematic block diagram of a second embodiment of a measuring device 1. In this second embodiment, the receptacles 2a, 2b each comprising an upper chamber 5a and a lower chamber 5b. The electrode structure 4a, 4b each is fixedly mounted at the bottom of the related lower chamber 5b. The upper chambers 5a are provided for storing the fluid culture medium 3a, 3b and for being placed in the related lower chamber 5b after inserting the fluid culture medium 3 into the related upper chamber 5a and optionally also into the lower chamber 5b. The upper chambers 5a are closed with a microporous membrane 10 at their bottom. When injecting biomass into the fluid culture medium 3, a biofilm 7 is growing within the upper chamber 5a. The biofilm 7 is floating on top of the fluid culture medium 3 and cells are hindered to reach the electrode structure 4a, 4b at the bottom of the respective lower chamber 5b and to adhere to said electrode structure 4a, 4b.

Thus, when inserting the upper chamber 5a in the corresponding lower chamber 5b, the fluid culture medium 3 will be placed on top on the electrode structure 4a and 4b and the biofilm 7 will grow in distance to the electrode structure 4a, 4b. The microporous membrane 10 has the effect of acting against cells adhering to the electrode structure 4a, 4b, so that interfering effects to the measurement result are reduced. The pore size of the microporous membrane 10 is, for this purpose, preferably smaller than the mean cell diameter.

Figure 3:
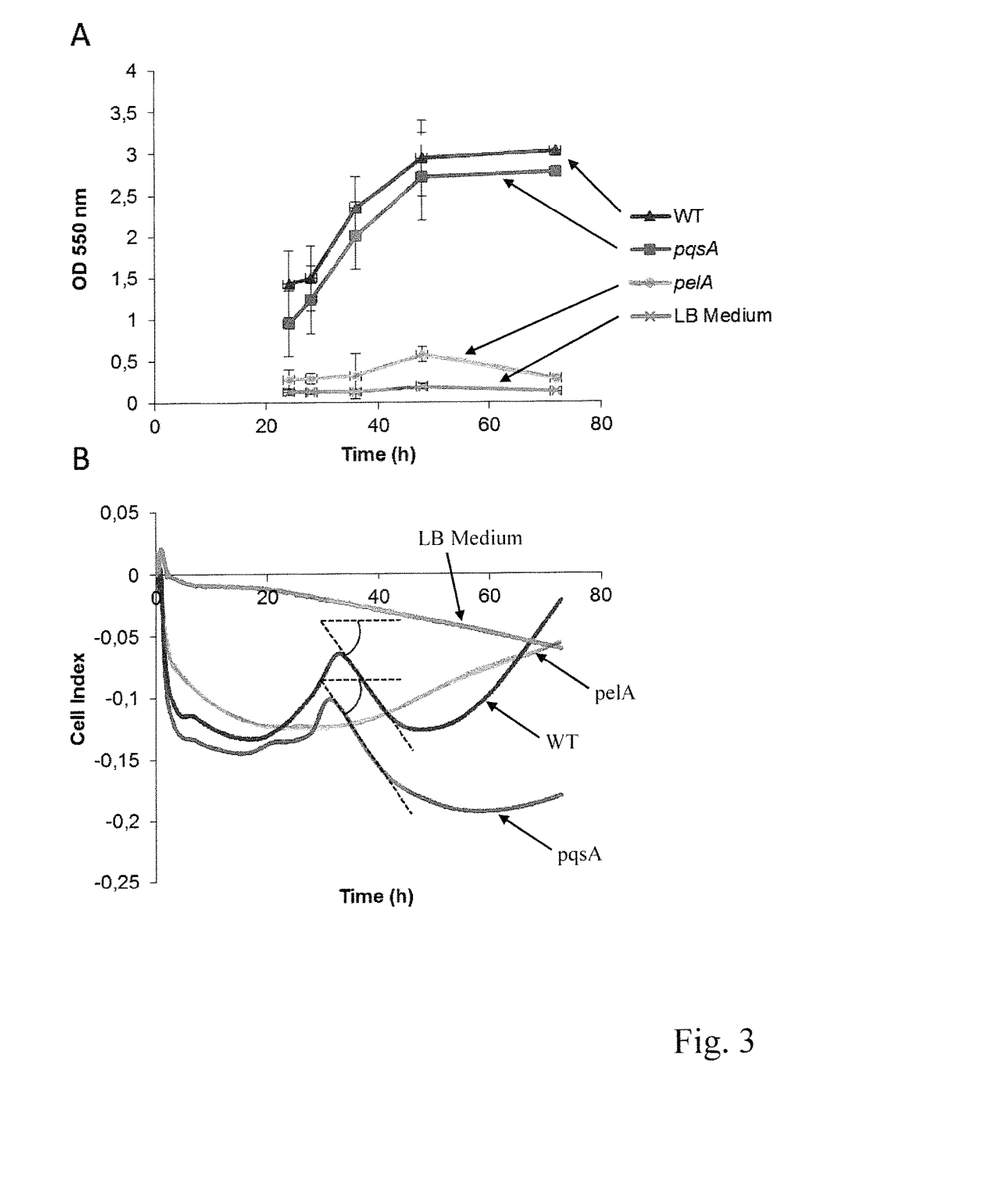
FIG. 3—Diagram of crystal violet (CV) by monitoring absorption at 550 nm staining measurements of biofilms formed by PA14 (wild type WT, ΔpelA, and ΔpqsA) in a fluid culture medium LB at various timepoints (FIG. 3A), compared to the cell index measurements (FIG. 3B) of these strains under equal conditions.

FIG. 3 shows a diagram of the cell index for biofilms of *Pseudomonas aeruginosa* measured by use of the impedance spectroscopy device xCELLigence® Real-time cell analyzer according to the prior art (FIG. 3B), in comparison to a standard method for biofilm quantification that is based on staining of the biofilm with crystal violet (FIG. 3A). The diagram shows that the characteristic change in cell index occurs at time periods (ca. 30-45 h) that are featured by significant growth of biofilm.

The experiment was repeated for a number of n with n=12 for the well type WT and pelA and pqsA mutants. For the medium control n was equal to 8. ΔpelA is a mutant of the wild type WT without the pelA gene, showing only planktonic growth of biofilm. ΔpqsA is a deletion mutant showing growth of biofilm with an increased capacity as compared to the wild type WT. ΔpelA grown within the fluid culture medium provides an almost horizontal line without significant reduction. Thus, there is no biofilm growing within this sample. With the ΔpelA probe it is also verified that the method according to the present invention is not sensitive for planktonic cells.

In the example according to diagram of FIG. 3, the cell index is calculated based upon the scaled impedance.

Figure 4:
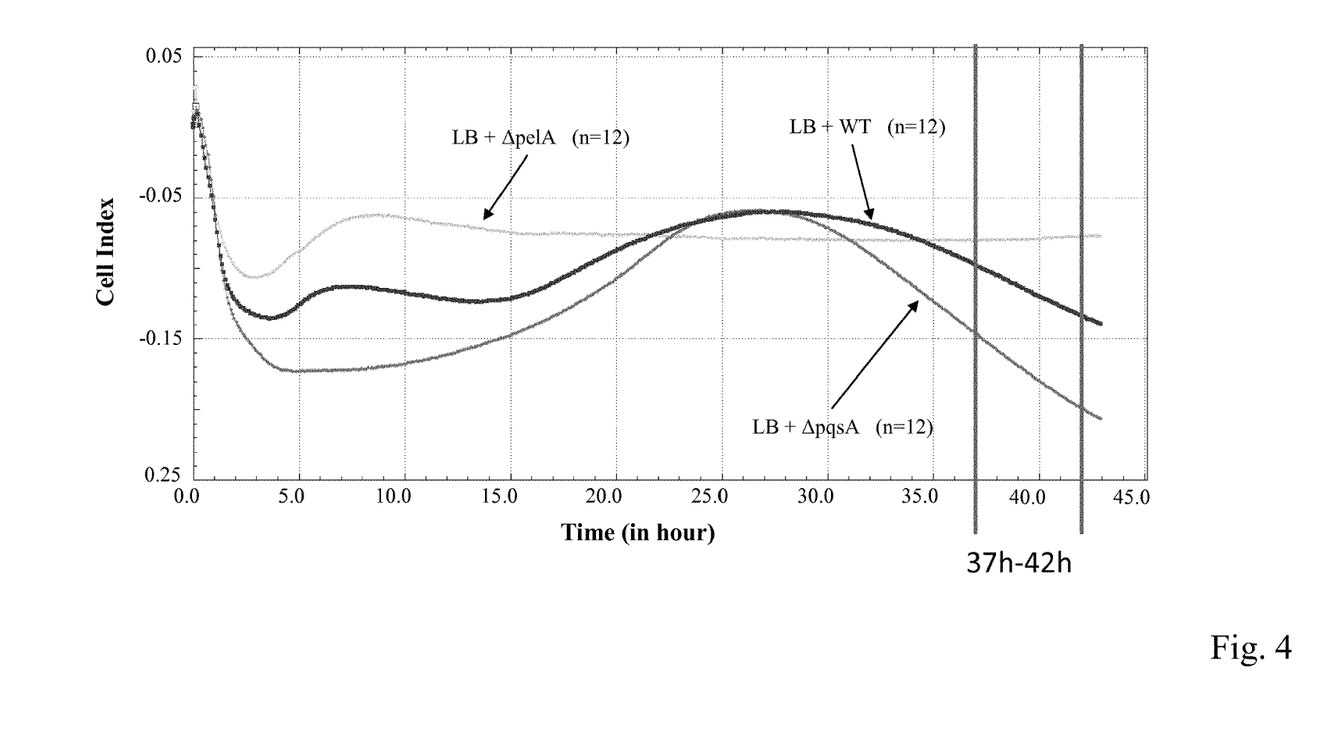
FIG. 4—Diagram of the cell index over the time for determining the PA14 biofilm growth rate in a fluid culture medium LB with ΔpelA, wild type WT and ΔpqsA.

FIG. 4 shows a diagram of the cell index over the time for a plurality of probes measured with the xCELLigence® Real-time cell analyzer for biofilm of *Pseudomonas aeruginosa*. The biomass *Pseudomonas aeruginosa* had been measured as an exemplary biomass. Eventually also other strains can be analyzed. The 96 E-Plate had been used for a measuring time of 43 hours. The fluid culture medium LB had been introduced into the receptacles together with wild type (WT) PA14, ΔpelA deletion mutant or ΔpqsA, respectively.

When placing a fluid culture medium LB between the electrode structure 4a, 4b and the biofilm 7, the value of the cell index shows a fast decrease within a starting phase, a following increase and, after expiration of the specific growth time, e.g. of ca. 20 hours, an almost linear decrease. A significant linear reduction of the negative cell index occurs after about 35 hours and more preferably in the time frame of the 37 hours to 42 hours. Within this time frame of 37 hours to 42 hours, the directional cell index RK=(cell index[t2]−cell index[t1])/(t2−t1) is decreasing. Thus, for such a short time frame, the value of the cell index change provides the directional cell index RK, which corresponds to the linear relation between the capacitance and the reactance having the general form of a straight line. Optionally, and in particular in case of evaluating longer time frames, the growth rate of biofilm can be calculated as function of the natural logarithm of the cell index, e.g. by the formula RK=ln(cell index[t2]−cell index[t1])/(t2−t1).

The directional cell index RK has, in this example, a value of −7.25E-03/h±7.56E-04 for the biofilm growth rate of WT.

For the biofilm growth rate of ΔpqsA, the directional cell, index RK has a value of −1.07E-02/h±1.01E-03.

The measurements had been taken for a number of 12 samples.

The biofilm growth rate can be determined according the impedance measurement with fluid culture medium placed between the electrode structure and the biofilm. The biofilm growth rate is proportional to the directional coefficient of the capacitance, e.g. the gradient of (Z) or (cell index) when considering the value of Z or the related cell index. For longer time frames linearizing by use of the natural, logarithm might be necessary, so that biofilm growth rate is proportional to the gradient of ln (Z) or ln (cell index).

Thus, the biofilm growth rate is directional proportional to (cell index($t2$)−(cell index($t1$)).

and for longer, time frames between t1 and t2 by use of the natural logarithm ln(cell index($t2$)−cell index($t1$)).

The variable t1 is the first time of the measurement window after a specific growth time e.g. 37 hours, while t2 is the end time of measuring time, e.g. 42 hours.

The cell index or impedance curve shows a continuous reduction within this time measurement time frame t1 to t2.

Figure 5:
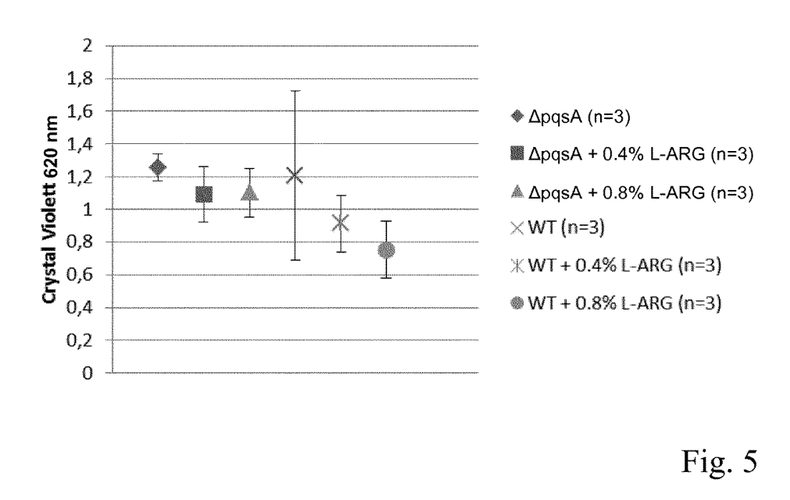
FIG. 5—Diagram of PA 14 biofilms determined after 43 hours with crystal violet by monitoring absorption at 620 nm.

FIG. 5 is a diagram of various types of PA14 biofilms measured by use of the 96-Well-Plate after 43 hours by use of the fluid culture medium LB with crystal violet analysis by monitoring absorption at 620 nm.

It is obvious that compared to the wild type WT alone, the addition of arginine (L-Arg) to the wild type WT inhibits the growth of biofilm.

Figure 6:
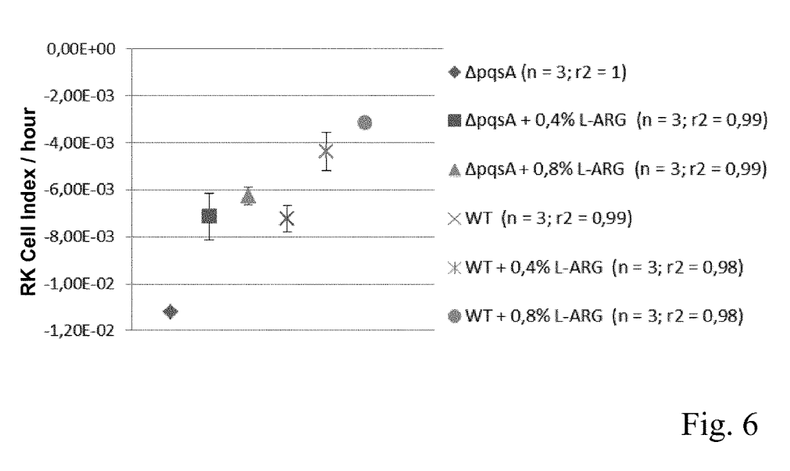
FIG. 6—Diagram of the RK cell index per hour for PA14 biofilms determined by impedance spectroscopy.

FIG. 6 shows a diagram of the RK cell indices obtained for various types of PA14 biofilms grown with the fluid culture medium LB by use of the impedance analysis with a 96-xCELLigence® Well-Plate within the evaluation time of 37 to 42 hours.

For ΔpqsA the highest negative RK cell index occurs, which is related to the biofilm growth rate. The use of 0.4% or 0.8% Arginine (L-Arg) reduces the biofilm growth rate by about ½.

Adding 0.4% or 0.8% Arginine (L-Arg) to the wild type WT results in reduction of the biofilm growth rate compared to the wild type WT without the presence of L-Arg. Again the directional cell index RK of about −0.004/h is directly proportional to the biofilm growth rate.

The factor r2 provides information on the average straightness of the line in the section considered for determining the biofilm growth rate.

As can be seen when comparing the diagrams in FIG. 5 and FIG. 6, the standard deviation can be significantly decreased and the distinctiveness can be increased by impedance analysis of the biofilm growth rate when measuring the reduction of the reactance with fluid culture medium between the biofilm and the electrode structure. The impedance analysis allows measuring of a plurality of probes in parallel within short time.

The measuring device can also be provided in front of an integrated circuit or integrated chip array.

In particular, the growth time of biofilm can be shortened by reducing the volume of the fluid culture medium 3 (LB). Due to the reduced volume cells reach earlier a threshold of cell density where they are going to produce biofilm.

FIGS. 3 and 4 shows that the growth of biofilm does not occur continuously but in different phases. The method for measuring the biofilm growth when the capacitance increases and the reactance decreases can not only be used for determining *Pseudomonas aeruginosa* PA14 biofilm growth. Other classes of biomaterials exhibit the same effect, in particular all ESKAPE organisms. ESKAPE pathogens are *Enterococcus faecium, Staphylococcus aureus, Klebsiella pneumoniae, Acinetobacter baumannii, Pseudomonas aeruginosa*, and *Enterobacter* species.

When monitoring the different phases of biofilm growth with their characteristic changes of the cell index curve over the measurement time, it is possible to define suitable times for taking probes of biomass from the receptacles in order to analyze the probe as required. Thus, the cell index curve over the time measured with the possible presence of biofilm floating on the fluid culture medium and not significantly adhering to the electrode structure provides an indicator for the appropriate timing of samples to be taken from the biofilm.

In order to probe the specific effect of the pellicle biofilm on the cell index, two experiments had been performed.

Figure 7:
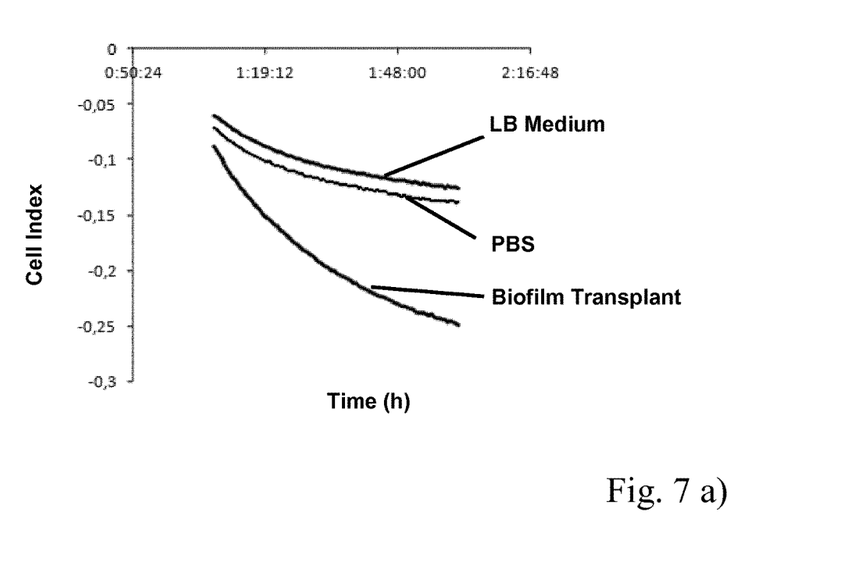
FIG. 7a)—Diagram of the cell index over the time for a control experiment after transplantation of biofilm, the addition of PBS and the LB medium as negative control.
FIG. 7b)—Diagram of the cell index over the time for an experiment where paraffin was also added in different amounts (10-100 μL) to wells (B) to mimic pellicle biofilm, given paraffin has no dielectric constant its presence showed no effect on the capacitance.

FIG. 7a) shows the result of the Cell index over the time measured with the Xcelligence® system, where Biofilm was transplanted to an adjacent receptacle with a metal loop to measure the effect of its presence on the impedance spectroscopy (n=4) compared to the addition of 10, 20, 40, and 80 µl PBS buffer (n=1)—the average value is shown—and no addition (LB medium, n=8).

FIG. 7b) shows the result of the Cell index over the time measured with the Xcelligence® system, where paraffin was also added in different amounts (10-100 µL) to wells (n=4) in order to mimic pellicle biofilm. The results were compared to the sole LB medium (n=8). Given paraffin has no dielectric constant its presence showed no effect on the capacitance.

First, a pellicle biofilm obtained by growing PA14 in LB medium for 72 h was transplanted, with a metal loop into wells filled with LB medium. In control experiments, PBS buffer was added to LB medium as shown in FIG. 7a).

Secondly, as shown in FIG. 7b), paraffin (10-100 µl) was added as an artificial substrate for comparison. Paraffin is immiscible with water and therefore floats on top of the hydrophilic medium due to its lower density. Because its chemical composition consists of alkanes, paraffin doesn't have a dielectric constant, in contrast to the pellicle biofilm of *P. aeruginosa*. For both experiments, the Xcelligence® system was calibrated once and paused before addition. It can be observed, that the slope of decrease after transplantation of biofilm was steeper than that obtained for an addition of PBS alone and the LB medium. This effect cannot be explained by the addition of an immiscible layer on top of the LB medium, as the addition of paraffin led to unchanged slopes of cell index.

Figure 8:
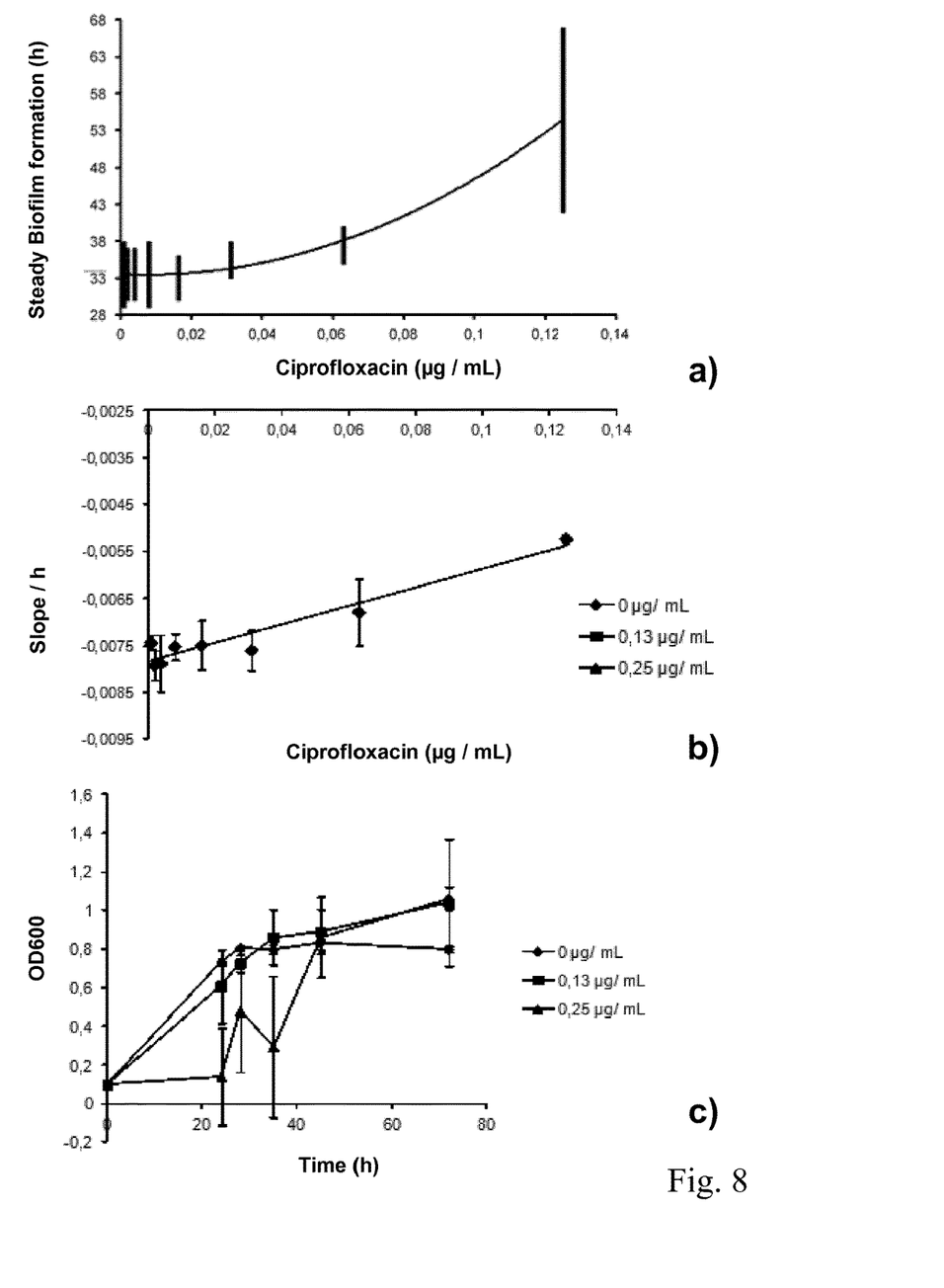
Figure 9:
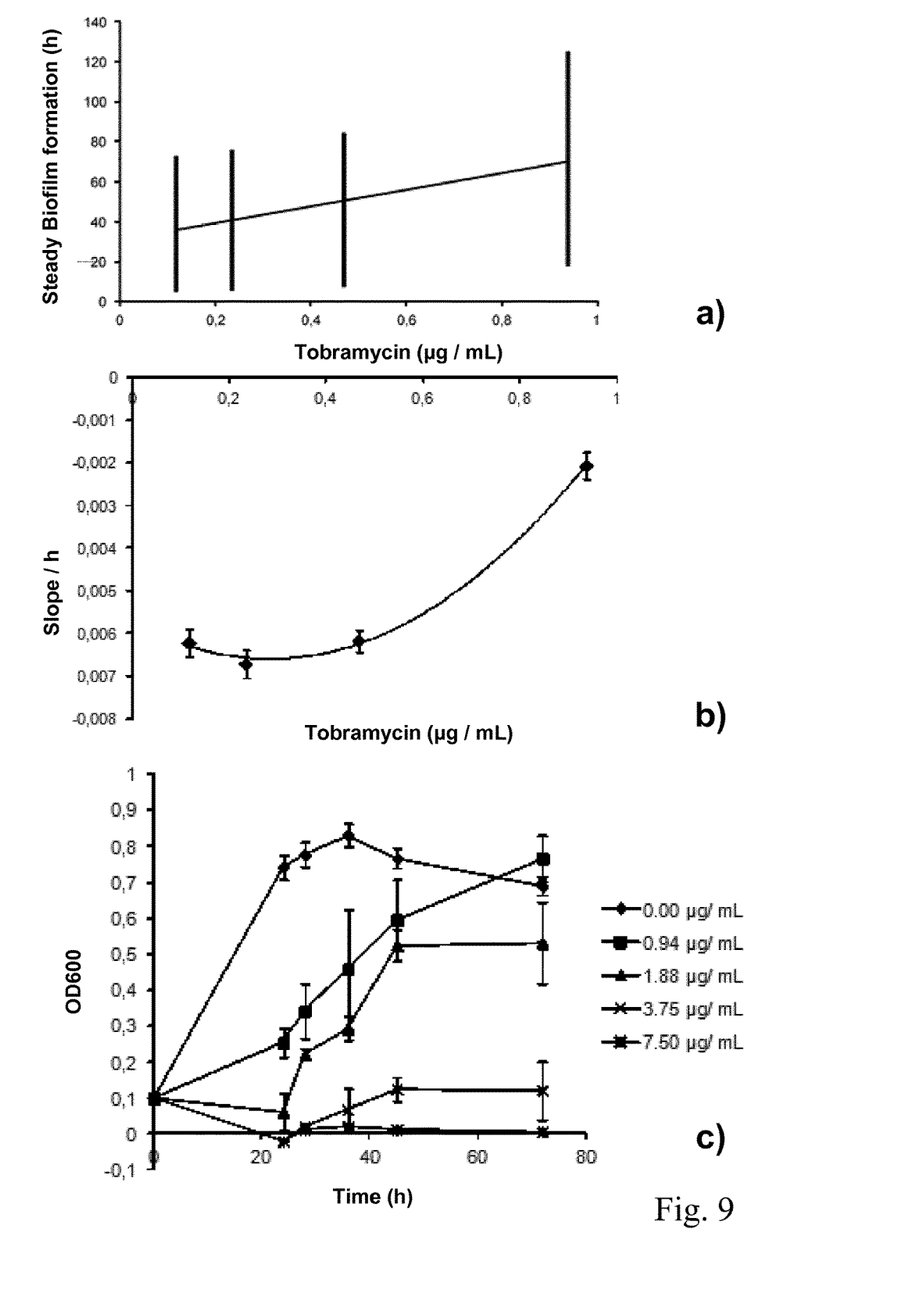
Figure 10:
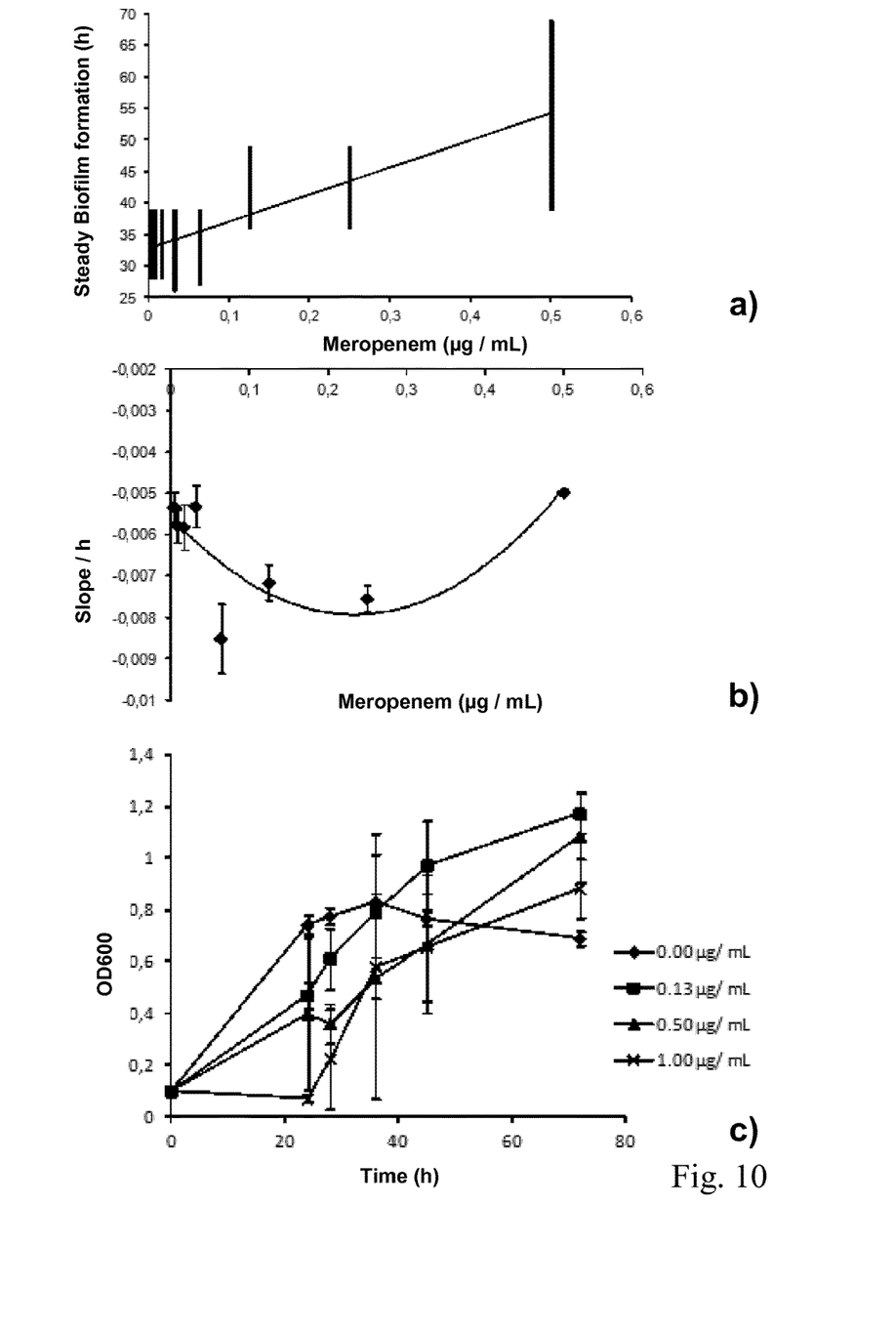

The impedance method has also been used to study the effect of antibiotics on biofilm formation of *P. aeruginosa* PA14. The results of the impact of ciprofloxacin (A), tobramycin (B), and meropenem (C) on biofilm formation of PA14 are shown in FIGS. 8 to 10. As examples, the antibiotics ciprofloxacin (FIGS. 8a)-c)), tobramycin (FIGS. 9a)-c)) and meropenem (FIGS. 10a)-c)) have been tested. All three antibiotics changed the impedance curves in a concentration-dependent manner, indicating effects on biofilm formation. Interestingly, impedance spectroscopy could monitor an effect on biofilm formation at antibiotic concentrations that did not impact planktonic growth at the same period of time. For example, the addition of 0.13 µg/mL ciprofloxacin clearly changed the impedance curve reflecting altered biofilm formation, although planktonic growth was not impaired at this concentration. At a concentration of 0.25 µg/mL, steady biofilm formation was not observed anymore, but planktonic growth was still possible.

The effect on impedance was quantified by three parameters at varying antibiotic concentrations:

The first parameter is the time of onset of a linear decrease of the cell index, (FIGS. 8a), 9a) and 10a)).

The second parameter is the duration of a linear decrease of the cell index. This duration was determined by a linear trendline that was fitted to the data with an $r^2$ value of 0.97 or higher. In the graphs of FIGS. 8a), 9a) and 10a), the black vertical bars represent the time period over which the biofilm formation rate was measured to be steady, based on a straight line assigned with an $r^2$ of at least 0.97 (n=3 or 4).

The third parameter was the cell index slope during that time period (FIGS. 8b), 9b) and 10b)). These graphs show the concentration dependency of the biofilm formation expressed in the slope/h of the cell index (n=3 or 4).

For ciprofloxacin and tobramycin, a shallower decline could be observed at increasing concentrations, indicating an impaired biofilm formation. For meropenem on the other hand, the increasing cell index slope suggests that it induced biofilm formation at concentrations between 0.063 and 0.25 µg/ml; this effect vanished at 0.5 µg/ml. Especially at the highest tested concentrations, all antibiotics led to later onsets of linear declines of impedance; at the same time, the period of linear decline was longer compared to untreated samples, indicating a delayed and attenuated biofilm formation.

FIGS. 8c) to 10c) show the result of the control experiment by measuring the OD600 value over the time with UV spectroscopy. OD600 indicates the absorbance, or optical density, of a sample measured at a wavelength of 600 nm and indicates the concentration of cells in a liquid. These graphs of FIGS. 8c), 9c) and 10c) represent growth curves of PA14 at various concentrations over time (n=4). At t=0 the OD600 was installed at 0.1.

The method allows determining the effect of other classes of modulators, for example
  standard of care drugs used for the treatment of *P. aeruginosa*, including aminoglycosides (e.g. Amikacin, Tobramycin) Fluorochinolones (e.g. Ciprofloxacin, Levofloxacin, Ofloxacin) beta-lactam antibiotics (e.g. Meropenem, Doropenem, Imipenem, Piperacillin, Cefepime);

Compounds that have shown activity against *P. aeruginosa* in vitro and/or in vivo models (e.g. POL7080, Eravacyclin, Omadacycline, Plazomicine, Ceftazidime-Avibactam, Ceftolozane/Tazobactam);

tool compounds with known positive or negative effects on of biofilm growth (e.g. arginine and casamino acid);

agonists and antagonists of quorum sensing (e.g. from the classes of AHL- or PQS-analogs);

Virulence factors (e.g. compounds interfering with secretion systems like anti-PcrV antibodies).

The results of the method for determining the growth of biofilm can be used to present online phenotypical effects of the biofilm growth. Thus, molecular changes can be made visible that are related to Membrane composition
Metabolites
Proteome
Transcriptome
Fluxome.

The invention claimed is:

1. A measuring device for determining a growth rate of biofilm, comprising:
    at least one electrode structure;
    an impedance measuring unit electrically connected or connectable to the electrode structure for measuring impedance of the electrode structure;
    at least one receptacle for storing a fluid culture medium, wherein the at least one receptacle is arranged for being coupled to the electrode structure such that the fluid culture medium is able to contact the electrode structure; and
    an evaluation unit arranged for determining the growth rate of biofilm, wherein a biofilm growth area is located or locatable at a distance from the electrode structure such that the fluid culture medium is between the electrode structure and the biofilm being grown, and wherein the evaluation unit evaluates growth of the biofilm as a function of a reduction rate of the impedance values measured on the electrode structure.

2. The measuring device according to claim 1, wherein the at least one receptacle comprises a chamber having a closed bottom, and the electrode structure is arranged at the bottom of the chamber in an internal space of the chamber.

3. The measuring device according to claim 1, wherein the at least one receptacle comprises
    an upper chamber,
    a lower chamber, and
    a microporous membrane between the upper chamber and the lower chamber, and
wherein the electrode structure is arranged adjacent to the microporous membrane in an interconnection area of the upper chamber and the lower chamber,
and
wherein the upper chamber is configured to store the fluid culture medium with the biofilm growing in the upper chamber.

4. The measuring device according to claim 1 wherein the electrode structure comprises a pair of comb-type finger electrodes, wherein fingers of the pair of comb-type finger electrodes are alternately arranged adjacent and at a distance from each other such that adjacent fingers extend in opposite directions from each other.

5. The measuring device according to claim 1 wherein the at least one receptacle includes a plurality of receptacles, wherein each receptacle of the plurality of receptacles comprises a pair of electrodes having a first electrode and a second electrode, and wherein at least two of the first electrodes are electrically interconnected to each other, and wherein the second electrodes are individually controllable by the impedance measuring unit.

6. The measuring device according to claim 1 wherein the evaluation unit is arranged for determining the growth rate of the biofilm by scaling the measured impedance values and determining the growth rate of the biofilm as a function of the reduction rate of the scaled impedance value.

* * * * *